United States Patent [19]

Paton et al.

[11] Patent Number: 5,356,668
[45] Date of Patent: Oct. 18, 1994

[54] FLUORINATING POLYMER SURFACES

[75] Inventors: Duncan M. Paton, Renfrewshire; Timothy R. Ashton, Ayrshire; Roshan Maini, Renfrewshire, all of Scotland

[73] Assignee: Vascutek Limited, Renfrewshire, Scotland

[21] Appl. No.: 917,088

[22] PCT Filed: Dec. 9, 1991

[86] PCT No.: PCT/GB91/02180
§ 371 Date: Aug. 4, 1992
§ 102(e) Date: Aug. 4, 1992

[87] PCT Pub. No.: WO92/10532
PCT Pub. Date: Jun. 25, 1992

[30] Foreign Application Priority Data

Dec. 7, 1990 [GB] United Kingdom ............... 9026687

[51] Int. Cl.⁵ ............................................. B05D 3/02
[52] U.S. Cl. ............................. 427/2.25; 427/393.5; 427/389.9
[58] Field of Search ............ 427/2, 322, 412.5, 389.9, 427/393.5; 623/1

[56] References Cited

U.S. PATENT DOCUMENTS

| | | | |
|---|---|---|---|
| 3,839,743 | 10/1974 | Schwarcz | 623/11 |
| 4,153,745 | 5/1979 | Hart | 427/244 |
| 4,167,045 | 9/1979 | Sawyer | 427/2 |
| 4,391,844 | 7/1983 | Baczek et al. | 427/236 |
| 4,413,074 | 11/1983 | Wrasidlo et al. | 427/246 |
| 4,414,280 | 11/1983 | Silva | 427/245 |
| 4,470,859 | 9/1984 | Benezra et al. | 427/243 |
| 4,902,290 | 2/1990 | Fleckenstein | 427/2 |
| 4,981,727 | 1/1991 | Brinduse et al. | 427/385.5 |
| 4,985,280 | 1/1991 | Scholz | 427/384 |
| 5,061,738 | 10/1991 | Solomon et al. | 427/2 |
| 5,171,611 | 12/1992 | Porter et al. | 427/245 |
| 5,242,995 | 9/1993 | Kim et al. | 623/1 |
| 5,246,451 | 9/1993 | Trescony et al. | 623/1 |

*Primary Examiner*—Shrive Beck
*Assistant Examiner*—Diana Dudash
*Attorney, Agent, or Firm*—Edward S. Irons

[57] ABSTRACT

Surfaces of polymers, particularly polyesters, can be fluorinated by deposition of a fluorocarbon from solution. The fluorocarbon may be an amorphous fluoropolymer, such as the copolymer of tetrafluoroethylene and bis-2,2-trifluoromethyl-4,5-difluoro-1,2-dioxole sold under the trademark TEFLON AF ®, which is soluble in fluorinated alkanes and other fluorinated liquids such as those sold under the trademark FLUORINERT ®. Surface-fluorinated polyesters, particularly in knitted fabric form, are useful as vascular grafts: the fluorinated surface reduces thrombogenicity and complement activation. The disadvantages of known surface fluorination methods, such as the cold plasma or glow discharge process, are avoided.

8 Claims, No Drawings

FLUORINATING POLYMER SURFACES

The subject of this invention is a process for modifying a surface on a polymer by forming a fluorinated surface on the polymer.

It frequently happens that an article made from a polymer which is particularly suitable for making that article displays undesirable characteristics or side effects when used in the environment to which the article is exposed. These characteristics may spring from so-called "active" atoms, which may principally be hydrogen or oxygen atoms, present in the molecules of a polymer. Vascular grafts are a case in point. Polymers in general, and polyesters in particular, are among the most suitable materials for use in making such a graft. Polymers such as polyester are, however, thrombogenic when exposed to blood as of course they are when used to form a vascular graft.

Blood platelets tend to adhere to the polymer and initiate blood clotting. Polymers such as polyester are also known to activate the blood complement system. This is undesirable as complement activation is one of the first stages of an inflammatory response to foreign material. There is therefore a need to modify the polymer surface to reduce its thrombogenicity and/or to reduce its platelet adhesion characteristics.

It has previously been proposed to eliminate or reduce the undesired surface activity of a polymer by fluorinating the polymer or at least its surface; this has been explained as replacing the active atoms in the polymer molecules, at the surface at least, by fluorine atoms.

One previously proposed method of fluorinating the surface of a polymer is disclosed in U.S. Pat. No. 4,264,750 and U.S. Pat. No. 4,404,256 and comprises exposing the polymer to a cold plasma containing ions and/or radicals of a fluorine-containing substance under conditions to cause substitution of hydrogen and/or other active atoms at the surface of the polymer with fluorine atoms. Other, similar, processes require the deposition of a thin layer of a fluoropolymer formed from the gaseous monomer through plasma discharge (Yasuda et al, *Biomat., Med. Dev., Art. Org.*, 4(3&4), 307-372 (1976) and Fowler et al, *The Third World Biomaterials Congress*, 21st to 25th Apr. 1988, Kyoto, Japan, Abstracts 2C1-35, page 99).

The known plasma and glow discharge processes require very close control, not only to provide effective fluorination but also to minimise the degradation of the polymer which always takes place as a result of such a treatment. It is also difficult to ensure a consistent surface coverage over all the bare polymer and, in the case of plasma polymerisation, the chemical structure of the deposited polymer is prone to variability and hence to having a hererogenous structure.

It might be thought that the problem could be avoided simply by preparing articles such as vascular grafts from a fluoropolymer, such as polytetrafluoroethylene (PTFE). In practice, however, this is not the case. Fabric grafts, particularly knitted ones, are preferred to those made of continuous, or microporous, material, to allow better tissue ingrowth once the graft is in situ in the patient. PTFE fabric grafts are prone to fraying as a result of yarn slippage caused by the low coefficient of friction of PTFE; this is an important consideration as fraying can cause the disruption of a sutured attachment of a graft to the host blood vessel.

The problem therefore still remains, and the present invention seeks to address it. It has now been found that a fluorine-containing layer can be deposited on a polymer without the need for the complex physico-chemical conditions of a plasma discharge process: instead, a fluoropolymer can be deposited from solution onto the underlying polymer.

According to a first aspect of the present invention, there is therefore provided a process for forming a fluorinated surface on a polymer, the process comprising dissolving a fluorocarbon in a solvent for the fluorocarbon, bringing the resulting solution into contact with the polymer and removing the solvent from the polymer.

By means of the invention, the polymer may present a non-active surface, for example a non-thrombogenic surface and/or a non-complement-activating surface. Alternatively or in addition, there may be little or no diffusion of fluorine-containing material into the bulk of the polymer, thus avoiding degradation of the polymer and preserving its original strength.

The term "fluorinated surface" should not be taken to imply that necessarily every single atom exposed at the surface is a fluorine atom. Rather, there will simply be a higher proportion of fluorine atoms at the surface, after the process of the present invention has been applied to a polymer.

By means of the invention, fluorinated surfaces can be applied to a wide variety of polymers (including polymer mixtures) for a correspondingly wide variety of uses. The invention has particular application, though, in the modification of polymers for use in surgically graftable material, particularly vascular grafts. Polyethylene and polypropylene, both of which are available from Montedison in yarn form, may be found to be suitable, but the most preferred polymers for use in vascular grafts are polyesters, particularly those sold under the trade marks KODAR (Kodak) TERYLENE (ICI) and DACRON (DuPont). Polyesters include but are not limited to polyethylene terephthalates (PETs) of general formula I:

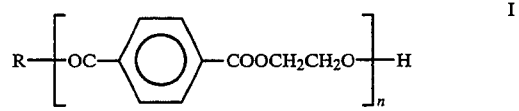

in which R represents a hydrogen atom or a $C_1$–$C_4$ alkoxy group (such as a methoxy group) and n represents an integer or other number indicative of the degree of polymerisation of the polymer. The polyester sold by DuPont Speciality Polymers Division (Wilmington, Del., USA) under the trade mark and designation DACRON TYPE 56 is the most preferred.

The physical form of the polymer will also vary depending on the nature and intended use of the article into which the polymer is (or is to be) made. For example, the polymer may be in the form of a sheet, film, strip, tube, shaped article, fabric piece (woven, knitted or other) or fabric article. Graftable materials, particularly vascular grafts, are preferably made from fabric, which for best results should be knitted rather than woven. For such materials, it is generally preferred for the process of the invention to be applied to the fabric piece or fabric article, rather than to the yarn from which the piece or article is made: in this way the problem of the modified surface being abraded when the yarn is woven or knitted is avoided. However, under some circumstances it may well be acceptable or even desirable for the yarn itself to be treated by the process of the invention.

The fluorocarbon which is coated onto the polymers by means of the process of the invention is preferably, but not necessarily, a fluoropolymer. Suitable monomers or prepolymers may be induced to form a fluoropolymer on the surface of the underlying polymer if required. The essential requirements of the fluorocarbon are that it be soluble, to a sufficient degree, in the solvent used and that it impart the desired characteristics to the surface of the underlying polymer when applied by the process of the invention (or that it be a useful precursor for imparting the desired characteristics).

It may not be necessary for the fluorocarbon only to contain the atoms fluorine and carbon, though it is likely that these atoms will predominant. Oxygen atoms may be present in some fluorocarbons, as may halogens other than fluorine, and hydrogen atoms are not necessarily excluded (although perfluorocarbons, in which fluorine atoms take the place of all hydrogen atom sites, are preferred). Fluorinated elastomers ("fluoro-elastomers") or fluorinated rubbers ("fluoro-rubbers") may be useful in the invention. Often they are soluble, at least in their prepolymer form if not in their fully polymerised or cross-linked form, in common solvents. The VITON ® fluorinated elastomer available from DuPont in prepolymer form is soluble in readily available solvents and can be coated onto a polymer substrate, whereupon it may be cross-linked to acquire the desired properties.

Among the fluorocarbons most preferred for use in the process of the present invention are amorphous fluoropolymers such as copolymers of tetrafluoroethylene and bis-2,2-trifluoromethyl-4,5-difluoro-1,2-dioxole. Such copolymers have the formula

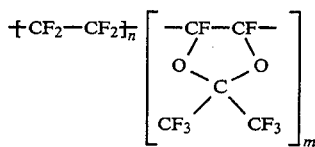

where n and m are integers or other numbers representative of the degree of polymerisation and of the proportions of the different monomeric units incorporated in the polymer. Such copolymers are available from DuPont under the trade mark TEFLON AF, which typically are soluble to the extent of from 2 to 15% (w/w) in certain solvents. The product TEFLON AF 1600 is preferred; the product TEFLON AF 2400 is also an appropriate one to use but is not quite so preferred as TEFLON AF 1600 because its solubility characteristics are not so favourable.

Mixtures of fluorocarbons can also be used in the process of the invention.

Solvents useful in the process of the invention are those in which the fluorocarbon is soluble to an acceptable degree and which do not have any unwanted effect on the polymer substrate. The nature of the solvent, whether a single component or a mixture, preferred for use will therefore depend primarily on the nature of the fluorocarbon to be deposited on the polymer substrate and, possibly, on the nature of the polymer substrate itself. As mentioned above, if the fluorocarbon is a fluorinated elastomer or fluorinated rubber, a wide variety of common solvents may be used; examples include methylethylketone, methylene chloride, carbon tetrachloride and others. If, as is preferred, the fluorocarbon is an amorphous fluoropolymer such as one of those sold under the trade mark TEFLON AF, then a fluorinated solvent may be used. Suitable fluorinated solvents include perfluoroalkanes (such as $C_6$–$C_{10}$ perfluoroalkanes, as exemplified by perfluorohexane ($C_6F_{14}$) and perfluoroheptane ($C_7F_{16}$)) perfluorocycloalkanes (such as $C_6$–$C_{10}$ perfluorocycloalkanes), which optionally may contain tertiary amino and/or ether functions. Fully fluorinated cyclic ethers and other perfluoro compounds may also be used.

Among the best fluorinated solvents are those available from 3M United Kingdom plc, Bracknell, Berkshire, under the FLUORINERT trade mark. These liquids, which are completely fluorinated organic compounds, were originally marketed for specialised applications in the electronics industry, but are particularly suitable for use in the present invention. The various FLUORINERT liquids vary in their physical and chemical characteristics. Those having a kinematic viscosity at 25° C. of 1.0 cs or below are preferred, as are those having an average molecular weight of 500 or below, and those having a vapour pressure of 10 torr and above. The FLUORINERT liquids satisfying these criteria include those known by the product designations FC-87, FC-72, FC-84, FC-77, FC-104 and, most preferred of all, FC-75.

The concentration of the fluorocarbon in the solvent may typically be in the range of 0.05% to 0.5% (w/w), with 0.075% to 0.2% (w/w) being preferred and about 0.1% (w/w) being optimal. Concentrations below 0.05% may in some circumstances not give completely reliable coverage, while at concentrations above 0.5% the amount of fluorocarbon may begin to affect the handling properties of the coated polymer in some instances.

The solution of the fluorocarbon in the solvent may be brought into contact with the polymer in any convenient way, depending on the nature of the polymer or the article formed from it. Immersion will often be preferred, but the solution may be sprayed or brushed onto the polymer if appropriate.

The contact time between the solution and the polymer is not particularly critical but should in general be sufficient to allow complete wetting of the polymer surface. A contact time of between 15 seconds and 1 minute (such as about 30 seconds) has been found to be quite adequate. It is preferred, though, for the polymer to be dipped in or otherwise brought into contact two or more times with the solution and to be allowed to dry between dippings. A better covering may be achieved this way. The time between dips will vary with drying conditions but at room temperature (25° C.) may be in the region of 10 to 60 minutes (for example about 30 minutes).

After contact (or final contact) with the solution, the polymer is dried to remove solvent. A drying time of from 10 to 60 minutes, as indicated above, is likely to be satisfactory at room temperature. The solvent may be recovered for future use if desired.

No particularly unusual conditions are needed for carrying out the process of the invention. For good adherence of the fluorocarbon to the polymer substrate, though, the polymer should be clean and free of grease.

This may be achieved by solvent cleaning either at room temperature or in a Soxhlet apparatus. Suitable cleaning solvents include chloroform, trichloroethylene or other chlorinated or chlorofluorinated solvents which do not have a deleterious effect on the polymer. As an alternative, plasma or glow discharge cleaning could be used (for example adapting the cold plasma processes known in the art and previously discussed): the adherence of the fluorocarbon to the polymer may be increased in this way.

For the invention to work optimally, the process should be carried out in a clean, particle-free environment. This will be routine, though, in the case of the production of surgical grafts such as vascular grafts.

As will be apparent from what has already been said, the invention has particular application in the production of vascular grafts, which are preferably constructed of knitted polyester yarn (although other porous structures can be used). After the graft has been knitted, and after the process of the invention has been applied to the graft, it is much preferred for the graft to be sealed prior to being packaged and sterilised. Sealing the graft prior to packaging enables the surgeon to dispense with the otherwise necessary step of sealing the graft by pre-clotting it with the patient's own blood. Collagen, albumin and alginate may be used to seal the graft, but it is preferred to use gelatin and, in particular, gelatin at least part of which has been treated to reduce the number of amino groups in it: such a sealing process is disclosed in EP-A-0183365. The gelatin coating serves to control the rate at which the graft becomes permeable.

The process of the invention can be accurately controlled to provide reproducible coatings on bare polymer structures. The chemical structure of the deposited fluorocarbon is homogeneous and physically it is hard and abrasion resistant.

A graft made by the process of the present invention consists basically of the pure polymer encased in a fluorocarbon coating which is not thrombogenic so that the graft has all the strength of the pure polymer but since the polymer is, in use of the graft, isolated from the blood passing through the graft it does not display the thrombogenicity of a graft made from the polymer alone.

According to a second aspect of the invention, there is provided an article, particularly a vascular graft, comprising a polymer on which a fluorocarbon has been deposited by solvent deposition.

The graft is preferably formed from fabric. Best results are obtained from the use of knitted fabric, particularly warp knitted fabric.

Other preferred features of the second aspect are as for the first aspect mutatis mutandis.

The invention will now be illustrated by the following examples.

EXAMPLE 1

Spools of DACRON TYPE 56 yarn (2×44/27) are placed in a Karl Meyer double bed Raschel knitting machine, where two fibres of yarn are warp knitted with 60 needles per inch into seamless long continuous (straight) vascular grafts of 8 mm internal diameter. The continuous grafts are then formed into same-sized lots and transferred to a Class 10,000 clean room. Here they are weighed, inspected for gross defects, washed and cut to 30 cm lengths. The grafts are externally supported by the application of a 0.9 mm APPRYL 3020 SM3 polypropylene helical coil melt bonded onto the outer surface. (APPRYL 3020 SM3 is a trade mark of Appryl SNC, Puteaux, France and is available from Ato Chemicals, Newbury, United Kingdom.) After the external support has been applied, the grafts are re-inspected, trimmed and then given a further inspection.

265.5 mg of TEFLON AF 1600 (copolymer of tetrafluoroethylene and bis-2,2-trifluoromethyl-4,5-difluoro-1,2-dioxole) powder, as supplied by DuPont, is dissolved in a plastic beaker in 150 ml of FLUORINERT FC75 fluorinated liquid, as supplied by 3M. The FLUORINERT FC75 liquid has a relative density at 25° C. of 1.77, so 150 ml of liquid weighs 265.5 g. The TEFLON AF 1600 powder is allowed to dissolve fully to produce a 0.1% (w/w) solution.

A 30 cm long, externally supported, knitted graft, as produced above, is dipped into the solution at room temperature for 30 seconds. Excess solution is removed and the graft is allowed to dry for 10 to 60 minutes in air. The graft is then re-dipped and finally dried.

Once dry, the fluorinated vascular graft is gelatin-sealed by following the procedure of Example 1 of EP-A-0183365 in a wet-process clean room. The sealed graft is then packaged and sterilised with ethylene oxide.

EXAMPLE 2

Using essentially the same knitting technology as is described in Example 1, a flat sheet of fabric is produced by knitting DACRON TYPE 56 yarn. The sheet is cut into 2.5 cm×2.5 cm squares, which are trimmed and inspected as given above in Example 1. The fabric squares are then coated with TEFLON AF 1600, as described in Example 1 above, and put aside for future use.

EXAMPLE 3

A 30 cm long, 8 mm internal diameter, vascular graft, as prepared in Example 1, was implanted as a thoracoabdominal bypass in a canine model. As a control, a similarly prepared but unfluorinated graft was also implanted. Both fluorinated and unfluorinated grafts were implanted for various lengths of time, ranging from 4 hours to 6 months; explants were then examined. Preliminary observations clearly demonstrated a more extensive cellular coating with endothelial-like cells of the luminal surface of the fluorinated grafts. For example, a fluorinated graft implanted for 1 month showed excellent healing with a smooth and glistening flow surface, with cells visible. In contrast, an untreated graft which had been implanted for six months still demonstrated red thrombi in the middle of the graft, even after that length of time.

EXAMPLE 4

Five 2.5 cm×2.5 cm pieces of fluorinated knitted fabric, as produced in Example 2, were incubated with 3 ml of heparinsed plasma, obtained from one of four human volunteers, for 1 hour. As a control, similar pieces of unfluorinated material were similarly tested. To assess the extent of complement activation, the levels of $iC_3b$ in the plasma were then estimated using a QUIDEL (trade mark) $iC_3b$ enzyme immunoassay. All test materials were pre-wetted by dipping twice in 100% absolute alcohol, twice in 50% alcohol, twice in distilled water and twice in isotonic saline. The results are shown in Table 1 below.

TABLE 1

| | iC$_3$b Values (μg/ml) | | | | Mean |
|---|---|---|---|---|---|
| | Volunteer number | | | | Values |
| | 1 | 2 | 3 | 4 | |
| Non-fluorinated Fabric | 11760 | 6990 | 4970 | 1050 | 6193 |
| Fluorinated Fabric | 3620 | 2450 | 1920 | 5390 | 3345 |

Although the results from volunteer number 4 are somewhat anomalous, the data overall clearly show a marked reduction of complement activation for the fluorinated fabric, when compared to the non-fluorinated fabric. Complement activation is believed to lead to hyperplasia, which can therefore be reduced by means of the present invention.

EXAMPLE 5

From 2.5 cm×2.5 cm fabric squares, as prepared in Example 2, were prepared 1 cm square fabric disks. As controls, non-fluorinated, but otherwise similar, fabric disks were prepared.

Freshly taken human blood, containing 10% (v/v) of 3.8% (w/v) tri-sodium citrate was spun for 15 minutes at 900 rpm in polystyrene centrifuge tubes. The platelet-rich plasma was removed using siliconised glass Pasteur pipettes and put into a polystyrene container, where it was allowed to rest for 1 hour at 37° C. An equal volume of filtered (0.2 μm) phosphate-buffered saline (PBS) was added.

To test each 1 cm square disk, 2 ml of the plasma/PBS mix and the disk were put into a 7 ml polystyrene bijou bottle, which was rotated gently for I hour at 37° C. After incubation, 0.5 ml of test or control plasma was taken and made up to 20 ml with filtered PBS. Platelets were counted on a COULTER ZM (trade mark) particle counter, on standard settings. The results were as follows:

| Non-fluorinated fabric | 43% depletion |
|---|---|
| Fluorinated fabric | 4% depletion |

The results show that grafts made from the fluorinated fabric are less likely to lead to platelet adhesion on the graft wall and therefore likely to be less thrombogenic than the untreated fabric.

We claim:

1. A process for forming a fluorinated surface on a polymer, the process comprising the steps of:
   a) forming a solution of perfluorocarbon in a solvent for the perfluorocarbon wherein the solvent is selected from the group consisting of perfluoroalkanes, perfluorocycloalkanes and mixtures thereof;
   b) bringing the solution into contact with the polymer surface; and
   c) removing the solvent from the solution in contact with the polymer surface.

2. The process as claimed in claim 1, wherein the solvent additionally contains a tertiary amine function.

3. The process as claimed in claim 1, wherein the solvent additionally contains a tertiary ether function.

4. A process for forming a fluorinated surface on a polymer, the process comprising the steps of:
   a) forming a solution of an amorphous fluorinated copolymer of tetrafluoroethylene and bis-2,2-trifluoromethyl-4,5-difluoro-1,2-dioxole, in a solvent for the amorphous fluorocarbon;
   b) bringing the solution into contact with the polymer surface; and
   c) removing the solvent from the solution in contact with the polymer surface.

5. A process as claimed in claim 1, wherein the polymer is in the form of a surgical graft.

6. A process as defined in claim 1, wherein the polymer is in the form of a vascular graft.

7. A process as claimed in claim 1, wherein the polymer is in the form of a surgical graft and wherein said graft is sealed after forming the fluorinated surface.

8. A process as claimed in claim 1, wherein the polymer is in the form of a surgical graft and wherein said graft is sealed with a gelatin after forming the fluorinated surface.

* * * * *